United States Patent [19]
Yoshida et al.

[11] Patent Number: 4,914,193
[45] Date of Patent: Apr. 3, 1990

[54] 5'-O-TRIORGANOSTANNYL DERIVATIVES OF DEOXYNUCLEOSIDES OR DEOXYNUCLEOTIDES AND THEIR USES

[75] Inventors: Tadao Yoshida, Aichi; Iwao Ohmori, Ichinomiya, both of Japan

[73] Assignee: Toagosei Chemical Industry Co., Ltd., Tokyo, Japan

[21] Appl. No.: 274,619

[22] Filed: Nov. 22, 1988

Related U.S. Application Data

[63] Continuation of Ser. No. 727,270, Apr. 25, 1985, abandoned.

[30] Foreign Application Priority Data

Jun. 8, 1984 [JP] Japan ............................. 59-116538
Aug. 27, 1984 [JP] Japan ............................. 59-176863

[51] Int. Cl.$^4$ ................. C07H 19/073; C07H 19/173
[52] U.S. Cl. .......................................... 536/23; 536/24; 536/26; 536/27; 536/28; 536/29
[58] Field of Search ................. 536/23, 24, 26, 27, 536/28, 29, 121

[56] References Cited

U.S. PATENT DOCUMENTS

| | | | |
|---|---|---|---|
| 2,609,368 | 9/1952 | Gaver | 536/121 |
| 3,227,707 | 1/1966 | Langer | 536/121 |
| 4,310,662 | 1/1982 | Crea | 536/28 |
| 4,474,947 | 10/1984 | Hudson et al. | 536/27 |

Primary Examiner—Ronald W. Griffin
Assistant Examiner—L. Eric Crane
Attorney, Agent, or Firm—Cooper & Dunham

[57] ABSTRACT

Novel triorganostannyl derivatives of deoxynucleosides or deoxynucleotides of the general formula:

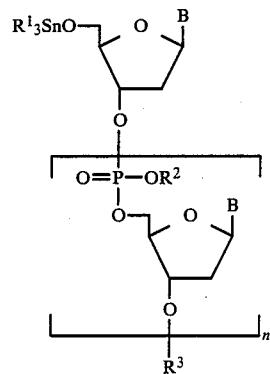

wherein $R^1$ is an alkyl or aryl group, $R^2$ is a protecting group, $R^3$ is a protecting group, B is a base residue which may have a protecting group, and n is zero or a positive integer and their amine salts are provided. They are prepared by reacting a deoxynucleoside or deoxynucleotide with either a triorganotin amide or a triorgano(alkoxy)stannane and may be useful as intermediates for the preparation of oligodeoxynecleotides.

3 Claims, No Drawings

5'-O-TRIORGANOSTANNYL DERIVATIVES OF DEOXYNUCLEOSIDES OR DEOXYNUCLEOTIDES AND THEIR USES

This is a continuation of application Ser. No. 727,270, filed Apr. 25, 1985, abandoned.

FIELD OF THE INVENTION

This invention relates to novel organotin compounds and their amine salts, processes for their preparation and their uses for the preparation of oligodeoxynucleotides. The novel organotin compounds according to this invention are characterized by the presence of a trialkylstannyl or triarylstannyl group substituted on the 5'-hydroxyl group of deoxynucleosides or deoxynucleotides and represented by general formula (I):

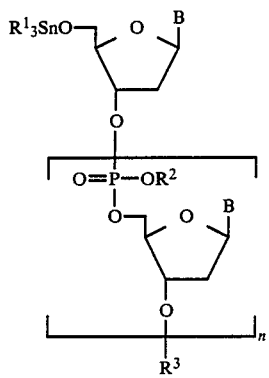
(I)

wherein $R^1$ is an alkyl or aryl group, $R^2$ is a protecting group, $R^3$ is a protecting group, B is a base residue which may have a protecting group, and n is zero or a positive integer.

BACKGROUND OF THE INVENTION

Organotin compounds have hitherto been investigated widely, among which several or more compounds have been put to practical applications as stabilizers for organic compounds or as pesticides. Among organotin compounds, those having one or more tin-oxygen bonds such as $R'_3SnOR''$, $R'_2Sn(OR'')_2$, $R'Sn(OR'')_3$ and $Sn(OR'')_4$ wherein $R'$ is an alkyl or aryl group and $R''$ is a hydrogen atom or an alkyl or aryl group have been reported in a number of literature and patent specifications. For example, Amberger et al. reported that the reaction of (diethylamino)trimethylstannane (II) with methanol gives (methoxy)trimethylstannane (III) according to the following equation:

$$Me_3SnNEt_2 + MeOH \longrightarrow Me_3SnOMe + HNEt_2$$
(II)                   (III)

[refer to Angew. Chem. Intern., Ed. Engl., 3, 138 (1964)].

Up to date, however, there exists no report on compounds of type $R'_3SnOR'''$ wherein $R'$ is an alkyl or aryl group and $R'''$ is a deoxynucleoside residue or a deoxynucleotide residue as far as we know.

We have investigated on the reaction of an organotin amide compound of general formula (IV):

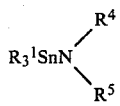

wherein one of $R^4$ and $R^5$ is an alkyl or aryl group and the other is a hydrogen atom or an alkyl or aryl group with a deoxynucleoside or deoxynucleotide of general formula (V):

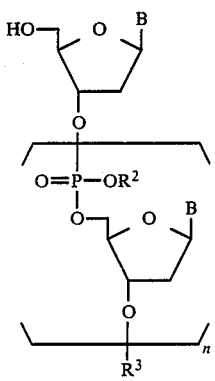

wherein $R^2$, $R^3$, B and n have the same meanings as defined above and now found that the reaction proceeds according to the reaction equation (1) to give a triorganostannyl derivative of deoxynucleoside or deoxynucleotide of general formula (I) or an amine salt thereof.

Reaction equation (1)

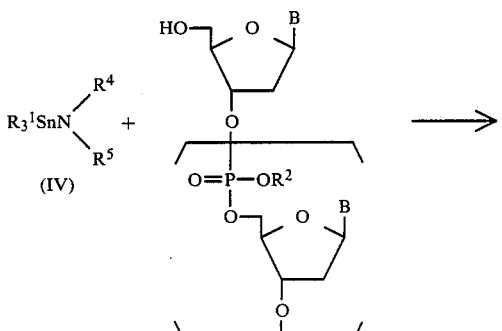

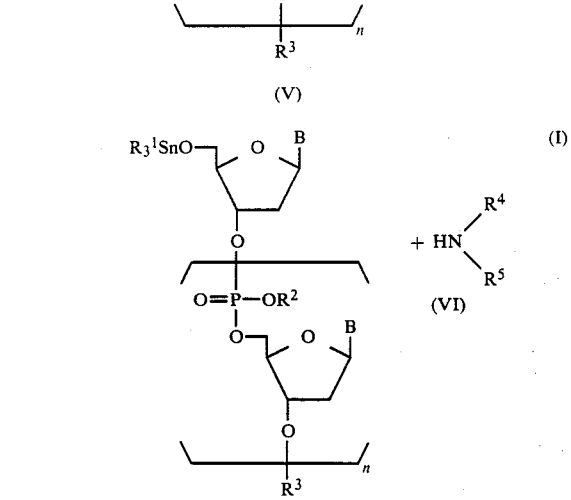

We have further found that the desired triorganostannyl derivative of deoxynucleoside or deoxynucleotide of general formula (I) can also be prepared by replacing the organotin amide compound of general formula (IV) above with a corresponding triorgano(alkoxy)stannane of general formula (VII):

$$R^1_3SnOR^6 \quad (VII)$$

wherein $R^6$ is a secondary or tertiary alkyl group or a 1-substituted cycloalkyl group according to the reaction equation (2).

Reaction equation (2)

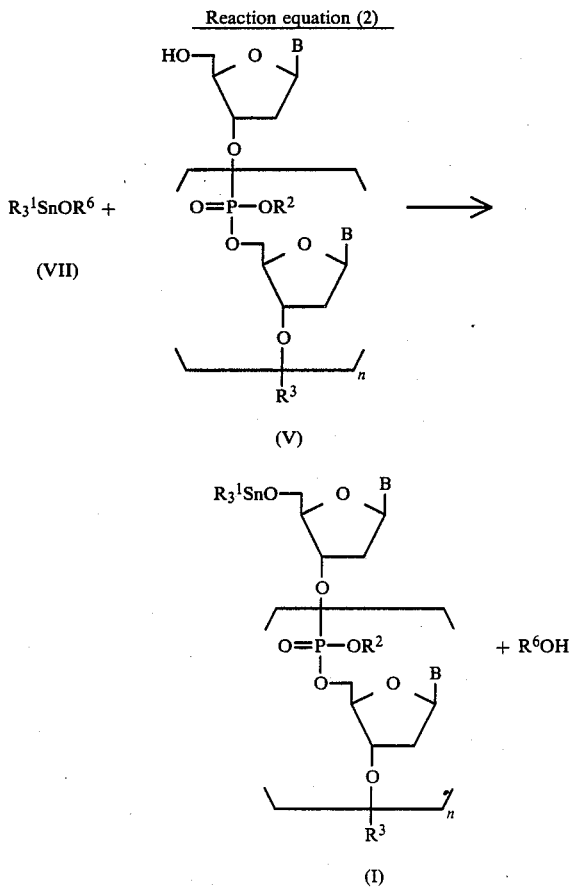

SUMMARY OF THE INVENTION

Accordingly, the primary object of this invention is to provide novel triorganostannyl derivatives of deoxynucleosides or deoxynucleotides of general formula (I) and their amine salts which are useful as intermediates for the preparation of oligodeoxynucleotides.

Another object of this invention is to provide processes for the preparation of the novel compounds of general formula (I) and their amine salts.

A further object of this invention is to provide a process for the preparation of oligodeoxynucleotides starting from the novel organotin compound of general formula (I).

These and other objects of this invention will become clear from the descriptions hereinafter given.

The first aspect of this invention therefore provides novel organotin compounds of general formula (I):

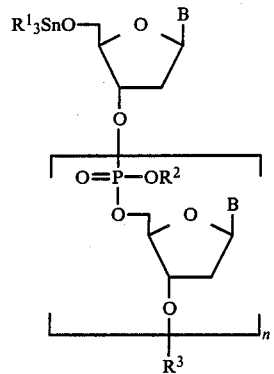

wherein $R^1$ is an alkyl or aryl group, $R^2$ is a protecting group, $R^3$ is a protecting group, B is a base residue which may have a protecting group, and n is zero or a positive integer and their amine salts.

The second aspect of this invention provides a process for the preparation of the organotin compounds of general formula (I) and their amine salts according to the reaction equation (1) above.

The third aspect of this invention provides another process for the preparation of the organotin compounds of general formual (I) according to the reaction equation (2) above.

The fourth aspect of this invention provides a new process for the preparation of oligodeoxynucleotides starting from the novel organotin compounds of general formula (I).

DETAILED DESCRIPTION OF THE INVENTION

In general formula (I) above, $R^1$ is preferably selected from a lower alkyl group and phenyl group, more preferably a lower alkyl group of 1~4 carbon atoms; $R^2$ is preferably selected from o-chlorophenyl and p-chlorophenyl groups; $R^3$ is selected from acetyl, benzoyl and t-butyldimethylsilyl groupus; and B is preferably selected from thymine, $N^2$-isobutyrylguanine, $N^4$-benzoylcytosine and $N^6$-benzoyladenine moieties.

The structural formulae of the residual groups given above as preferred B group are as follows:

Thymine moiety
(abbreviated as T)

$N^4$-Benzoylcytosine moiety
(abbreviated as Cbz)

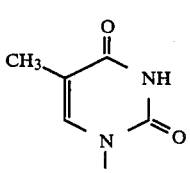  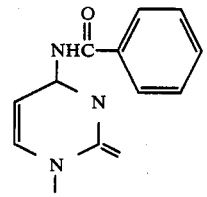

-continued

N²-Isobutyrylguanine moiety (abbreviated as Gib)

N⁶-Benzoyladenine moiety (abbreviated as Abz)

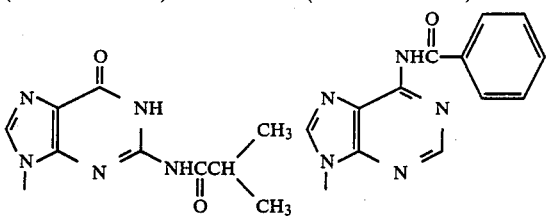

In the first process for the preparation of organotin compounds of general formula (I) according to the reaction equation (1) above, the desired 5'-O-triorganostannyl derivative of deoxynucleoside (n=0 in general formula (I)) can be identified by $^1$HNMR spectrum or $^{13}$CNMR spectrum in the form of an amine salt formed with amine compound (VI) produced as a by-product as shown in the reaction equation (1) (see Table 1 hereinafter given). Summary of the identification is as follows:

(a) $^1$HNMR or $^{13}$CNMR spectrum of the reaction product obtained by the reaction between triorganostannylamide compound of general formula (IV) and deoxynucleoside of general formula (V) wherein n=0 shows disappearance of the proton of 5'-hydroxyl group ($\delta 4.0 \sim 5.0$ ppm) of deoxynucleoside of general formula (V) wherein n=0 and appearance of a signal of amine compound of general formula (VI).

(b) In the $^1$HNMR or $^{13}$CNMR spectrum discussed in (a) above, all the other signals than the signal of amine compound of general formula (VI) correspond to the structure of 5'-O-triorganostannyldeoxynucleoside of general formula (I) wherein n=0.

According to the reaction equation (1) above, 5'-O-triorganostannyldeoxynucleotide of general formula (I) wherein n≠0 is also produced in the form of an amine salt which is demonstrated by $^1$HNMR spectrum thereof (see Table 1 hereinafter given).

The triorganostannyl derivatives of deoxynucleosides of general formula (I) are unstable in water. This is clearly shown by $^1$HNMR spectrum thereof. For example, 5'-O-triethylstannyl-3'-O-t-butyldimethylsilyl-thymidine obtained by the reaction between 3'-O-t-butyldimethylsilylthymidine of general formula (V) wherein n=0, R³ is t-butyldimethylsilyl group and B is thymine moiety and (diethylamino)triethylstannane of general formula (IV) wherein R¹, R⁴ and R⁵ each are ethyl group decomposes within 5 minutes upon addition of an equimolar proportion of heavy water as shown by $^1$HNMR spectrum thereof.

In the second process for the preparation of organotin compounds of general formula (I) according to the reaction equation (2) above, the formation of the desired triorganostannyl derivative of deoxynucleoside of general formula (I) wherein n=0 in a quantitative yield can be confirmed by measuring $^1$HNMR spectrum of an amine salt thereof after the conversion thereto. For instance, triethyl(t-butoxy) stannane is reacted with 3'-O-t-butyldimethylsilyl-thymidine in equimolar proportion in an organic solvent such as methylene chloride or 1,2-dichloroethane and after the completion of reaction, the solvent and t-butanol are removed from the reaction mixture under reduced pressure and an equimolar proportion of diethylamine is added to the remaining reaction product. $^1$HNMR spectrum of the resulting solution shows disappearance of both the absorption bands for 5'-hydroxyl group ($\delta 3.18$ ppm, triplet, J=5.0 Hz) of the 3'-O-t-butyldimethylsilyl-thymidine and for t-butoxy group ($\delta 1.18$ ppm, singlet) of the triethyl(t-butoxy)stannane and the quantitative formation of diethylamine salt of 3'-O-t-butyldimethylsilyl-5'-O-triethylstannylthymidine.

In the preparation of organotin compounds and their amine salts according to the processes of this invention, the reaction according to either the reaction equation (1) or (2) is preferably carried out in an inert solvent. Although such an inert solvent may be methylene chloride, 1,2-dichloroethane, benzene, ether, tetrahydrofuran, p-dioxane, pyridine and the like, it is preferred to use a solvent easy to be dehydrated and purified, such as methylene chloride, 1,2-dichloroethane or benzene, particularly those obtained by drying over phosphorus pentoxide for about 12 hours followed by subjecting to distillation, because the intended reaction must be conducted in a dehydrated system. The reaction may be carried out at a temperature in the range of 0°~35° C., but is desirably effected at room temperatures because no special measure such as cooling or heating is required for those temperatures. Since the reaction may proceed rapidly, no special care is necessary for the reaction time, that is about 5~15 minutes may be sufficient for the completion of reaction at room temperatures.

Among organotin amide compounds of general formula (IV) to be used as starting compound in the first process according to the reaction equation (1), those having as substituent R¹ a lower alkyl group such as methyl, ethyl, propyl or butyl may preferably be used because they are easily isolatable by distillation, although any of those having as R¹ an alkyl or aryl group as defined above may be used. Similarly, substituents R⁴ and R⁵ in the organotin amide compounds of general formula (IV) each may be any of an alkyl or aryl group or a hydrogen atom, but are most preferably a lower alkyl group having up to 5 carbon atoms in view of ease in synthesis and good stability of such compounds. Desirably, the organotin amide compounds isolated by distillation from reaction mixture are stored under dry nitrogen or argon atmosphere because they are somewhat unstable to water and carbon dioxide though they have a high thermal stability.

In carrying out the reaction according to reaction equation (1) above, it is preferred to use 1~1.1 moles of the organotin amide compound of general formula (IV) per 1 mole of the deoxynucleoside or deoxynucleotide.

Among triorgano(alkoxy)stannanes of general formula (VII) to be used as starting compound in the second process according to the reaction equation (2), those having as substituent R¹ a lower alkyl group such as methyl, ethyl or n-butyl may preferably be used in view of the facile isolation and purification by distillation, although any of those having as R¹ an alkyl or aryl group as defined above may be used. As substituent R⁶ in the triorgano(alkoxy)stannanes of general formula (VII), there may be used a secondary alkyl group such as i-propyl or s-butyl; a tertiary alkyl group such as t-butyl, t-amyl, tri-t-butylmethyl or tricyclohexylmethyl; and a 1-substituted cycloalkyl group such as 1-methylcyclohexyl or 1-cyclohexylcyclohexyl, among which a tertiary alkyl or 1-substituted cycloalkyl group is preferred because of a high reactivity thereof.

The triorgano(alkoxy)stannanes of general formula (VII) may be prepared by a known reaction between a triorganotin chloride of general formula (VIII) and a metal alkoxide of general formula (IX) according to the reaction equation (3):

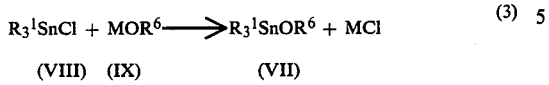

wherein $R^1$ and $R^6$ have the same meanings as defined above and M is an alkali metal (refer, for example, to G. P. Mack, U.S. Pat. No. 2,745, 820).

In deoxynucleosides or deoxynucleotides of general formula (V) to be used as another starting compound in both the first and second processes of this invention according to the reaction equations (1) and (2) respectively, the protecting group of the base residue B, 3'-hydroxyl-protecting group $R^3$ and phosphate ester-protecting group $R^2$ may be those known to be suitably used in chemical syntheses of oligodeoxynucleotides. Typical examples of the protecting group of the base residue B include benzoyl, anisoyl and isobutyryl groups. Those of the 3'-hydroxyl-protecting group $R^3$ may include acetyl, benzoyl and t-butyldimethylsilyl groups and those of the phosphte ester-protecting group $R^2$ may include phenyl, o-chlorophenyl and p-chlorophenyl groups. Compounds of general formula (V) having these substituents may be prepared by a known method as for example described by C. B. Reese in Tetrahedron, 34, 3143 (1978) (also refer to the references cited therein).

The molar proportions of the compound of general formula (V) and the compound of general formula (VII) used in the reaction of equation (2) may vary from 1:1 to 1:10, but it is advisable not to use an excess amount of compound of general formula (VII) from economical point of view. Usually, equimolar proportion of the two compounds are used. The reaction between compound of general formula (V) and compound of general formula (VII) may usually be carried out in such solvent as shown above at room temperature for 5~15 minutes, after which the solvent is removed and replaced by another solvent suitable for the preparation of oligodeoxynucleotides.

The second process of this invention according to the reaction equation (2) is preferred to the first process according to the reaction equation (1) because the starting compound of general formula (VII) is much more stable to water and carbon dioxide than the starting compound of general formula (IV). Thus, the former compound (VII) can be stored in a nitrogen atmosphere at $-20°$ C. for a long period of time (about one year), whereas the latter compound (IV) cannot.

The triorganostannyl derivatives of deoxynucleosides or deoxynucleotides of general formula (I) and their amine salts according to this invention are useful as intermediates for the preparation of oligodeoxynucleotides.

According to the fourth aspect of this invention as shown hereinbefore, therefore, there is provided a process for the preparation of oligodeoxynucleotides of general formula (X):

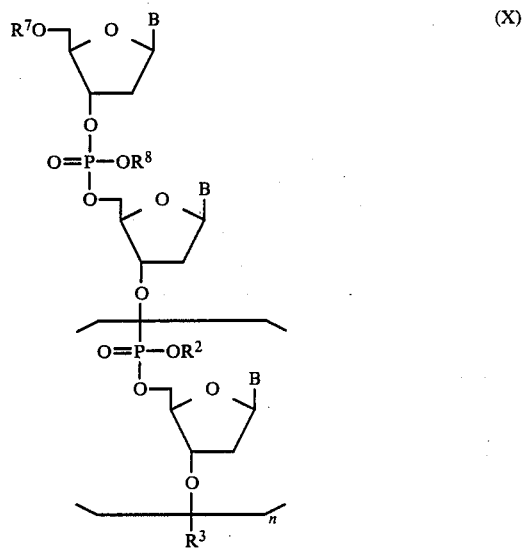

wherein $R^7$ is a protecting group, $R^8$ is a protecting group and $R^2$, $R^3$, B and n have the same meaniangs as defined above which comprises reacting a triorganostannyl derivative of deoxynucleoside or deoxynucleotide of general formula (I):

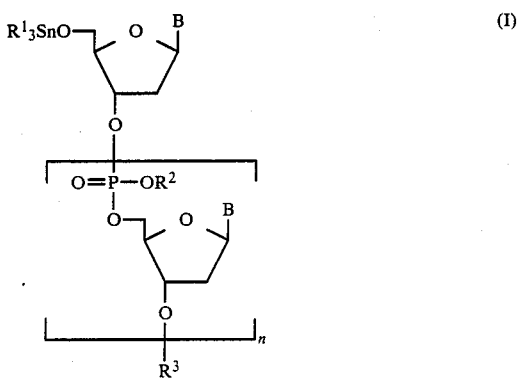

wherein $R^1$, $R^2$, $R^3$, B and n have the same meanings as defined above or an amine salt thereof with a deoxynucleotide of general formula (XI):

wherein $R^7$, $R^8$ and B have the same meanings as defined above and X is a leaving group of nitrogen-containing five-membered cyclic type.

The protecting group $R^7$ may typically be t-butyldimethylsilyl, 4,4'-dimethoxytrityl, 4-monomethoxytrityl or trityl group. 4,4'-Dimethoxytrityl or 4-monomethoxytrityl group is preferred as it is removable easily and selectively with an acid or a Lewis acid. The protecting group $R^8$ may typically be phenyl, o-chlorophenyl or p-chlorophenyl group, o-chlorophenyl group being the best for its easily removable nature on the action of an oxamate. The leaving group X being a nitrogen-containing five-membered cyclic type may typically be imidazolyl, triazolyl or benzotriazolyl group. The most preferred leaving group X is triazolyl group.

Deoxynucleotide of general formula (XI) to be used for the preparation of oligodeoxynucleotides according to the fourth aspect of this invention, hereinafter referred to as compound (XI), may be prepared easily and in high yield by reacting a deoxynucleoside of general formula (XII):

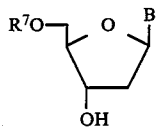
(XII)

wherein $R^7$ and B have the same meanings as defined above with a phosphorus-nitrogen-containing five-membered cyclic compound of general formula (XIII):

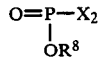
(XIII)

wherein $R^8$ and X have the same meanings as defined above in an inert solvent. As inert solvent, there may be used an ether solvent such as tetrahydrofuran, 1,4-dioxane and the like as is already known, but methylene chloride has been found the best as inert solvent in the preparation of compound (XI) for various reasons. Thus, methylene chloride is inexpensive, easily dehydratable and purifiable and gives a high yield of the desired product which is obtained in the form of a methylene chloride solution which may be used as it is, without isolating compound (XI) therefrom, for the preparation of oligodeoxynucleotides of general formula (X) according to this invention. Further, the phosphorus-nitrogen-containing five-membered cyclic compound of general formula (XIII) may also be prepared in methylene chloride as solvent, as hereinafter explained, and then used in the form of a resulting methylene chloride solution directly for the preparation of compound (XI).

The deoxynucleosides of general formula (XII) may easily be prepared, as already known in the art, by a deoxynucleoside of general formula (XIV):

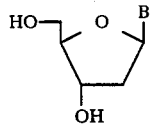
(XIV)

wherein B has the same meaning as defined above with trityl chloride, methoxytrityl chloride or dimethoxytrityl chloride. Those of general formula (XII) wherein $R^7$ is dimethoxytrityl group are commercially available.

The phosphorus-nitrogen-containing five-membered cyclic compounds of general formula (XIII) may easily be prepared by reacting an arene phosphorodichloridate of general formula (XV):

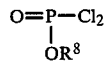
(XV)

wherein $R^8$ has the same meaning as defined above with imidazole, triazole or benzotriazole in methylene chloride in the presence of a base such as triethylamine. The resulting reaction product, the phosphorus-nitrogen-containing five-membered cyclic compound of general formula (XIII) in the form of a methylene chloride solution, may be used as such, without isolating compound (XIII) therefrom, as starting material for the preparation of compound (XI). The methylene chloride solution of compound (XIII) can be stored under a dry atmosphere at $-20°$ C. for about 3 weeks and is therefore useful as phosphorylating agent for deoxynucleosides.

Dideoxynucleotides, hereinafter referred to as compound ($X_o$), which correspond to oligodeoxynucleotides of general formula (X) wherein $n=0$ may be prepared easily and in high yield according to this invention by reacting compound (XI) prepared as abovementioned with a new deoxynucleoside which corresponds to compounds of general formula (I) wherein $n=0$, hereinafter referred to as compound ($I_o$), or an amine salt thereof in methylene chloride at a temperature of $0° \sim 35°$ C. The reaction time may vary depending upon the molar proportions of compound (XI) and compound ($I_o$) and the nature of substituent X of compound (XI), but the completion of the reaction may easily be determined by thin layer chromatography and the like. Thus, in case where compound (XI) wherein $R^7$ is dimethoxytrityl group is used, the progress of the reaction may conveniently monitored by taking a chromatogram in a thin layer chromatography and slowly heating spots on the chromatogram from the back thereof up to $300°-400°$ C. at which dimethoxytrityl group gives rise to a brown color. Such method of coloration of dimethoxytrityl group is advantageous over those hitherto used such as one relying on the use of an acid such as sulfuric acid because the former gives a uniform color easily distinguishable, whereas the latter gives a thin or uneven color which is hard to distinguish exactly. After the completion of the reaction, the desired compound ($X_o$) may be purified by a column chromatography to isolate it in a high yield of the order of 95%.

Trideoxynucleotides which correspond to oligodeoxynucleotides of general formula (X) wherein $n=1$ may be obtained easily and in high yield according to this invention by reacting a compound corresponding to general formula (I) wherein $n=1$, hereinafter referred to as compound ($I_1$), with compound (XI) in methylene chloride at a temperature of $0° \sim 35°$ C. The reaction time may vary depending upon the molar proportions of compound (XI) and compound ($I_1$) and the nature of substituent X of compound (XI). It is therefore desirable to monitor the progress of the reaction by thin layer chromatography for determining the completion of the reaction.

Higher oligodeoxynucleotides corresponding to general formula (X) wherein $n=N$ (N is an integer of at least 2) may be prepared, according to this invention, in a manner similar to the above-mentioned by reacting a compound corresponding to general formula (I) wherein $n=N$, hereinafter referred to as compound ($I_N$) with compound (XI). Compound ($I_N$) may be prepared in the same manner as described above by selectively removing the protecting group $R^7$ of a compound (X) wherein n=N-1 followed by reacting the resulting compound with an organotin amide compound of general formula (IV).

Thus, according to this invention, it is possible to prepare long chain oligodeoxynucleotides of general formula (X) wherein n=10 or higher in a decreased number of reaction steps and in high yield We have further found that the reaction between compound (I) and compound (XI) for the preparation of oligodeoxynucleotides of general formula (X) may be promoted in the presence of an amine of general formula (XVI):

$$HNR^9R^{10} \quad (XVI)$$

wherein $R^9$ and $R^{10}$ each are alkyl group or $R^9$ and $R^{10}$ together with the adjacent nitrogen atom form piperidino group which may be substituted by one or more alkyl groups. Such a process thus constitutes a preferred embodiment of the fourth aspect of this invention.

According to our findings, the secondary amines of general formula (XVI) with higher acid dissociation constant (pKa), i.e. with higher basicity, are more effective for the acceleration of the said reaction. Typical examples of such secondary amines include di-n-propylamine, di-i-propylamine, di-n-butylamine, di-i-butylamine, di-t-butylamine, piperidine, 2,6-dimethylpiperidine, 2,2,6,6-tetramethylpiperidine and the like.

Any of these amines either prepared by a known method or commercially available may be used, preferably after having been dehydrated sufficiently with a suitable drying agent.

In the reaction between compound (I) and compound (XI), the molar proportion of the amine of general formula (XVI) to compound (I) used may preferably be 1:5~20.

The following Examples further illustrate, but not limit this invention. Examples 1 to 7 illustrate the preparation of organotin compounds of general formula (I) or their amine salts of this invention by the first process according to the reaction equation (1). Examples 8 to 15 illustrate the preparation of organotin compounds of general formula (I) or their amine salts of this invention by the second process according to the reaction equation (2). Examples 16 to 31 illustrate the preparation of oligodeoxynucleotides of general formula (X) by reacting compound (I) with compound (XI) according to the process of this invention.

EXAMPLE 1

Deuteromethylene chloride ($CD_2Cl_2$; 0.3 ml) was added to 3'-O-t-butyldimethylsilylthymidine (107 mg, 0.3 mmol) and the mixture was well stirred to give a homogeneous solution. To the solution was added (diethylamino)triethylstannane (83 mg, 0.07 ml, 0.3 mmol) at room temperature and the mixture was stirred at that temperature for 15 minutes to proceed the following reaction in substantially quantitative yield.

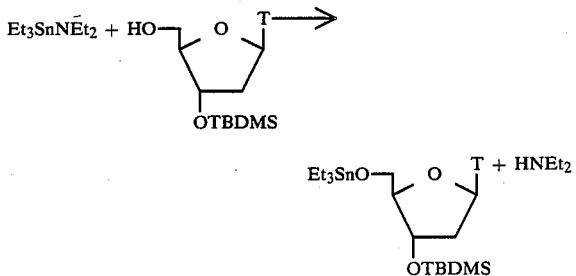

wherein Et is ethyl group; T is thymine residue and TBDMS is t-butyldimethylsilyl group.

$^1H$ and $^{13}C$ nuclear magnetic resonances of the reaction mixture were immediately measured. Results of $^1H$ NMR and $^{13}C$ NMR are given below. $^1H$ NMR ($CD_2Cl_2$, TMS) δ: 0.10 (s, 6H, Si($CH_3$)$_2$), 0.92 (s, 9H, SiC($CH_3$)$_3$), 1.09 (t, 6H, J=7.0 Hz, N($CH_2CH_3$)$_2$), 1.28 (s, 15H, SnEt$_3$), 1.85 (s, 3H, 5), 2.12~2.28 (m, 2H, 2'), 2.62 (q, 4H, J=7.0 Hz, N($CH_2CH_3$)$_2$), 3.60~3.96 (m, 3H, 4' & 5'), 4.28 (s, 2H, 3 & HNEt$_2$), 4.36~4.60 (m, 1H, 3'), 6.24 (t, 1H, J=7.0 Hz, 1') and 7.63 (s, 1H, 6) ppm. $^{13}C$ NMR ($CD_2Cl_2$, TMS) δ: −4.7, −4.6 (Si($CH_3$)$_2$), 7.6 (Sn($CH_2CH_3$)$_3$), 10.3 (Sn($CH_2CH_3$)$_3$), 13.1 (5-$CH_3$), 15.2(N($CH_2CH_3$)$_2$), 18.3 (SiC($CH_3$)$_3$), 26.0 (SiC($CH_3$)$_3$), 41.4 (2'), 44.0 (N($CH_2CH_3$)$_2$), 62.1 (5'), 72.7 (3'), 85.9 (1'), 88.6 (4'), 110.1 (5'), 136.7 (6), 154.2 (4) and 168.6 (2) ppm.

EXAMPLES 2~7

The procedure of Example 1 was repeated except that (dimethylamino)tri-n-butylstannane was used in place of (diethylamino)triethylstannane (Example 2) and/or a variety of deoxynucleosides were used in place of 3'-O-t-butyldimethylsilylthymidine (Examples 2~6) or a deoxynucleotide was used in place of 3'-O-t-butyldimethylsilylthymidine (Example 7). Corresponding 5'-O-triorganostannyldeoxynucleoside or 5'-O-triorganostannyldeoxynucleotide was obtained in the form of amine salt in a quantitative yield. Details of the starting compounds used, reaction product and $^1H$ NMR spectrum of the reaction product in each of Examples 2-7 are shown in Table 1, in which abbreviations used have the following meanings:

Me: methyl, Et: ethyl, Bu: butyl, Ac: acetyl.

T, Gib, Cbz, Abz and TBDMS have the meanings as given hereinbefore.

TABLE 1

| Example No. | Starting compounds | | | $^1H$ NMr spectrum of the reaction product ($CD_2Cl_2$, TMS): δ(ppm) |
|---|---|---|---|---|
| | Compound (IV) | Compound (V) | Reaction product | |
| 2 | Et$_3$SnNEt$_2$ |  | | 1.09(t,6H,J=7.0Hz,N($CH_2CH_3$)$_2$), 1,28(s, 15H,Sn($C_2H_5$)$_3$,1.85(s, 3H,5-$CH_3$),2.04(s,3H,COC$H_3$), 2.22-2.48(m,2H,2'),2.62(q,4H, J=7.0Hz,N($CH_2CH_3$)$_2$),3.72-4.00 (m,2H,5'),4.00-4.16(m,1H,4'), 4.42(s,2H,HNEt$_2$ & 3), 5.24-5.40(m,1H,3'),6.30(t,1H,J=7.0Hz, 1') and 7.71(s,1H,6) |

TABLE 1-continued

| Example No. | Starting compounds | | | ¹H NMr spectrum of the reaction product (CD₂Cl₂, TMS): δ(ppm) |
|---|---|---|---|---|
| | Compound (IV) | Compound (V) | Reaction product | |
| 3 | (n-Bu)₃SnNMe₂ | HO-[sugar-T, O-TBDMS] | n-Bu₃SnO-[sugar-T·HNMe₂, O-TBDMS] | 0.10(s,6H,Si(C$\underline{H}$₃)₂),0.80–1.20 (m,18H with a singlet at 0.92, SiC(C$\underline{H}$₃)₃ & Sn(C$\underline{H}$₂CH₂CH₂CH₃)₃), 1.20–1.80(m,18H,Sn(CH₂C$\underline{H}$₂C$\underline{H}$₂ CH₃)₃),1.88(s,3H,5-C$\underline{H}$₃), 2.22(t,J=7.0Hz, 2H,2′),2.40 (s,6H,N(C$\underline{H}$₃)₂),3.60–4.00(m,3H, 4′ & 5′),4.40(s,2H,$\underline{H}$,$\underline{H}$NMe₂ & 3),4.44–4.64(m,1H,3′),6.32(t, 1H,J=7.0Hz,1′) and 7.74(s, 1H,6) |
| 4 | Et₃SnNEt₂ | HO-[sugar-Gib, O-TBDMS] | Et₃SnO-[sugar-Gib·HNEt], O-TBDMS | 0.12(s,6H,Si(C$\underline{H}$₃)₂),0.92(s,9H, SiC(C$\underline{H}$₃)₃),1.12(t,6H,J=7.0Hz, N(C$\underline{H}$₂CH₃)₂),1.24(s,15H,Sn(C₂H₅)₃) 2.14–2.44(m,1H,—CC$\underline{H}$=),2.52–2.52–3.20 (m,6H,with a quadruplet at 2.70, J=7.0Hz,2′ & N(C$\underline{H}$₂CH₃)₂),3.64– 3.92(m,2H,5′),3.92–4.08(m,1H,4′), 4.56–4.76(m,1H,3′).6.28(t,1H, J=7.0Hz,1′),6.96(s,3H,$\underline{H}$NEt₃ & 2-N$\underline{H}$) and 8.08(s,1H,8) |
| 5 | Et₃SnNEt₂ | HO-[sugar-Cbz, O-TBDMS] | Et₃SnO-[sugar-Cbz·HNEt₂, O-TBDMS] | 0.10(s,6H,Si(C$\underline{H}$₃)₂),0.92(s,9H, SiC(C$\underline{H}$₃)₃),1.05(t,6H,J=7.0Hz, N(C$\underline{H}$₂CH₃)₂),1.08–2.72(m,6H,with Sn(C₂$\underline{H}$₅)₃),2.04–2.72(m,6H,with a quadruplet at 2.60,J=7.0Hz, 2′ & N(C$\underline{H}$₂CH₃)₂),3.60–4.20(m,3H, 4′& 5′),4.40–4.68(m,3H,with a singlet at 4.47,3′,$\underline{H}$NEt₂ & NH), 6.22(t,1H,J=6.0Hz,1′),7.14(d, 1H,J=7.0Hz,5),7.26–7.64(m,3H, Ph),7.88–8.10(m,2H,Ph) and 8.66 (d,1H,J=7.0Hz,6) |
| 6 | Et₃SnNEt₂ | HO-[sugar-Abz, O-TBDMS] | Et₃SnO-[sugar-Abz·HNEt₂, O-TBDMS] | 0.12(s,6H,Si(C$\underline{H}$₃)₂),0.96(s,9H, SiC(C$\underline{H}$₃)₃),1.04(t,6H,J=7.0Hz, N(C$\underline{H}$₂CH₃)₂),1.04–1.40(m,15H Sn(C₂$\underline{H}$₅)₃),2.20–2.96(m,6H,with a quadruplet at 2.58,J=7.0Hz, 2′ & N(C$\underline{H}$₂CH₃)₂),3.60–4.20(m, 3H,4′ & 5′),4.64–4.84(m,1H,3′), 5.24(s,2H,$\underline{H}$NEt₂ & NH),6.36– 6.60(m,1H,1′),7.24–7.60(m,3H,Ph), 7.62–8.00(m,2H,Ph) and 8.04– 8.70(m,2H,with a singlet at 8.60,2 & 8) |
| 7 | Et₃SnNEt₂ | HO-[sugar-T, O-P(=O)(O-chlorophenyl)-O-sugar-T, O-TBDMS] | Et₃SnO-[sugar-T·HNEt₂, O-P(=O)(O-chlorophenyl)-O-sugar-T, O-TBDMS] | 0.10(s,6H,Si(C$\underline{H}$₃)₂),0.92(s,9H, SiC(C$\underline{H}$₃)₃),1.10(t,6H,J=7.0Hz, N(C$\underline{H}$₂CH₃)₂),1.18(s,15H,Sn(C₂$\underline{H}$₅)₃), 1.86(s,6H,5-C$\underline{H}$₃ × 2),2.10–2.80 (m,8H,with a quadruplet at 2.66, J=7.0Hz,2′,2′ & N(C$\underline{H}$₂CH₃)₂3.60– 4.80(m,7H,5′,5′,4′,4′ & 3′), 5.04(s,3H,$\underline{H}$NEt₂,NH & NH),5.25– 5.50(m,1H,3′),6.38(t,1H,J=7.0Hz, 1′),6.44(t,1H,J=7.0Hz,1′),7.10– 7.70(m,5H,6 & Ph) and 7.76(s, 1H,6) |

EXAMPLE 8

3′-O-t-butyldimethylsilylthymidine (0.178 g, 0.5 mmol) was dissolved in 1,2-dichloroethane (1 ml) and triethyl (t-butoxy)stannane (0.140 g, 0.5 mmol) was added to the resulting solution. The solution obtained was stirred at room temperature for 5 minutes whereby to proceed the following reaction.

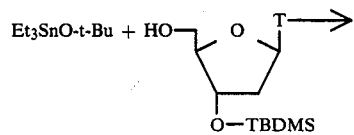

-continued

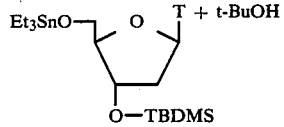

The reaction solution was distilled in vacuo to remove the 1,2-dichloroethane solvent and t-butanol therefrom. Deuteromethylene chloride (0.5 ml) and diethylamine (0.037 g, 0.05 mmol) were added to the residue obtained to convert the product to its diethylamine salt and the resulting solution was tested by $^1$H NMR which showed the same spectrum as that given in Example 1.

EXAMPLES 9 TO 15

The procedure of Example 8 was repeated using various triorgano(alkoxy)stannane and/or various deoxynucleosides or deoxynucleotides and/or various amines as given in Table 2 in which Am is amyl, 1-Mehex is 1-methylhexyl, Pr is propyl and Bz is benzoyl. The product obtained and $^1$H NMR spectrum thereof in each Example are also shown in Table 2.

TABLE 2

| Example No. | Starting compounds | | Amine | Reaction product | $^1$H NMR spectrum of the reaction product (CD$_2$Cl$_2$,TMS): δ(ppm)* |
|---|---|---|---|---|---|
| | Compound (VII) | Compound (V) | | | |
| 9 | Et$_3$SnO-t-Bu | 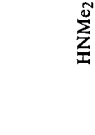 | HNEt$_2$ |  | The spectrum was the same as that given in Example 2. |
| 10 | n-Bu$_3$SnO-t-Am | 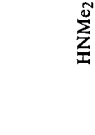 | HNMe$_2$ |  | The spectrum was the same as that given in Example 3. |
| 11 | Me$_3$SnO(1-Mehex) | 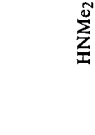 | HN-i-Pr$_2$ |  | 0.10(s,6H,Si(CH$_3$)$_2$),0.59(bs,9H, Sn(CH$_3$)$_3$),0.90(s,9H,SiC(CH$_3$)$_3$), 1.06(d,6H,J=7.0Hz,CH(CH$_3$)$_2$), 1.88(s,3H,5),2.22(t,2H,J=7.0Hz 2'),2.92(h,2H,J=7.0Hz,CH(CH$_3$)$_2$), 3.64(s,2H,HN(i-Pr)$_2$ & 3),3.65-4.00(m,3H,4' & 5'),4.40-4.65 (m,1H,3'),6.22(t,1H,J=7.0Hz,1'), 7.58(s,1H,6) |
| 12 | Me$_3$SnO-t-Bu | 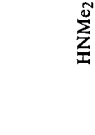 | HN-i-Pr$_2$ |  | 0.10(s,6H,Si(CH$_3$)$_2$),0.51(bs,9H, Sn(CH$_3$)$_3$),0.92(s,9H,SiC(CH$_3$)$_3$), 1.06(d,6H,J=7.0Hz,CH(CH$_3$)$_2$), 2.00-2.70(m,2H,2'),2.92(h,2H, J=7.0Hz,CH(CH$_3$)$_2$),3.60-4.10(m, 3H,4' & 5'),4.40-4.60(m,1H,3'), 4.76(bs,2H,HN(i-Pr)$_2$ & 3),6.24 (t,1H,J=6.0Hz,1'),7.10-7.70 (m,4H,5 & Ph),7.80-8.20(m,2H, Ph),8.50-9.00(m,1H,6) |
| 13 | Et$_3$SnO-t-Bu | 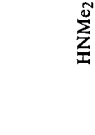 | HNEt$_2$ |  | 1.00-1.50(m,27H,with a singlet at 1.21,N(CH$_2$CH$_3$)$_2$, CH(CH$_3$)$_2$ & Sn(C$_2$H$_5$)$_3$), 2.40-3.20 (m,7H,with a quadruplet at 2.70,J=7.0Hz,CH(CH$_3$)$_2$ 2' & N(CH$_3$)$_2$),3.80-4.00(m, 2H,5'),4.20-4.35(m,1H,4'),5.55-5.70(m,1H,3'),6.32(t,1H,J=7.0Hz, 1'),7.01(s,3H,HNEt$_2$,NH & 1), 7.15-7.60(m,3H,Ph),7.80-8.00 (m,2H,Ph),8.08(s,1H,8) |

TABLE 2-continued

| Example No. | Starting compounds | | Amine | Reaction product | $^1$H NMR spectrum of the reaction product (CD$_2$Cl$_2$,TMS): δ(ppm)* |
|---|---|---|---|---|---|
| | Compound (VII) | Compound (V) | | | |
| 14 | Et$_3$SnO-t-Am | [structure: HO—sugar ring with Abz, O, O—TBDMS] | HNEt$_2$ | [structure: Et$_3$SnO—sugar ring with Abz, O, O—TBDMS · HNEt$_2$] | The spectrum was the same as that given in Example 6 |
| 15 | Et$_3$SnO-t-Bu | [structure: HO—sugar-T with phosphate linkage to Cl-phenyl and sugar-T-O—TBDMS] | HNEt$_2$ | [structure: Et$_3$SnO—sugar-T with phosphate linkage to Cl-phenyl and sugar-T-O—TBDMS · HNEt$_2$] | The spectrum was the same as that given in Example 7 |

*In Examples 11 and 12, the NMR data given are $^1$H NMR (CDCl$_3$,TMS): δ(ppm).

EXAMPLE 16

A dideoxynucleotide was prepared according to the following reaction.

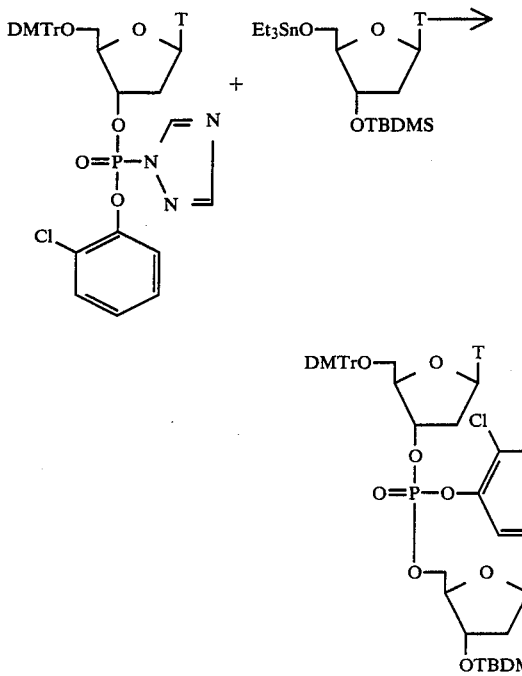

DMTr: dimethoxytrityl group

A methylene chloride solution of diethylamine salt of 5'-O-triethylstannyl-3'-O-t-butyldimethylsilyl-thymidine which was obtained by stirring (diethylamino)-triethylstannane (58 mg, 0.05 ml, 0.21 mmol) and 3'-O-t-butyldimethylsilyl-thymidine (71 mg, 0.2 mmol) in methylene chloride (0.2 ml) for 15 minutes according to the procedure of Example 1 was added at 20° C. to a methylene chloride solution of 5'-O-dimethoxytrityl-thymidine-3'-O-(2-chlorophenyl)phosphoro-1,2,4-triazolide which was obtained by adding pyridine (0.02 ml) and a methylene chloride solution of 2-chlorophosphoro-di-1,2,4-triazolide (0.8M, 0.36 ml, 0.288 mmol) to 5'-O-dimethoxytrityl-thymidine (131 mg, 0.24 mmol), stirring the mixture at 20° C. for 15 minutes, adding a solution of water in pyridine (1M, 0.012 ml, 0.012 mmol) to the reaction mixture and further stirring the mixture at room temperature for 15 minutes. The resulting mixture was stirred at 20° C. for 30 minutes to conduct the reaction. After the completion of the reaction was confirmed by a thin layer chromatography (hereinafter referred to as TLC), a 50% aqueous pyridine solution (0.5 ml) was added to the reaction mixture. The organic layer separated was extracted with methylene chloride (10 ml) and the extract was washed with a 0.5M aqueous potassium primary phosphate solution (10 ml) and with a 0.1M aqueous triethylammonium bicarbonate buffer (pH 7.5, 10 ml), successively, and then distilled in vacuo to remove the methylene chloride. The residue was subjected to a silica gel column chromatography using chloroform-methanol (40:1 by volume) as an eluent. The eluate was concentrated and the residue was dissolved in a small amount of methylene chloride. The methylene chloride solution was added dropwise to vigorously stirred n-hexane to deposit white crystals which were separated by filtration and dried to yield 2-chlorophenyl 5'-O-(dimethoxytrityl) thymidine-3'3'-O-(t-butyldimethylsilyl)thymidine-5' phosphate (206 mg). Yield was 96% calculated on 5'-O-triethylstannyl-3'-O-t-butyldimethylsilyl-thymidine.

TLC: Rf=0.67 (CHCl$_3$:MeOH=9:1)

$^1$H NMR (CDCl$_3$, TMS) δ(ppm): 0.08 (s, 6H, Si(CH$_3$)$_2$), 0.90 (s, 9H, SiC(CH$_3$)$_3$), 1.41 (s, 3H, 5-CH$_3$), 1.85 (s, 3H, 5-CH$_3$), 2.0–2.80 (m, 4H, 2' & 2'), 3.20–3.60 (m, 2H, 5'), 3.80 (s, 6H, OCH$_3$ & OCH$_3$), 3.90–4.70 (m, 5H, 3', 4', 4' & 5'), 5.30–5.50 (m, 1H, 3'), 6.29 (t, 1H, J=7.0 Hz, 1'), 6.50 (t, 1H, J=7.0 Hz, 1'), 6.80–7.00 (m, 4H, Ph), 7.10–7.80 (m, 15H, 6, 6 & Ph) and 9.72 (s, 2H, NH & NH).

EXAMPLES 17–24

The procedure of Example 16 was repeated using various deoxynucleotides and/or various 5'-O-triorganostannyl derivatives of deoxynucleosides or deoxynucleotides. Corresponding dideoxynucleotide or trideoxynucleotide was obtained in each Example. Details of the starting compounds used, reaction time, reaction product and yield and properties of the reaction product in each Example are given in Table 3.

The starting compound (I), an amine salt of 5'-O-triorganostannyl derivative of deoxynucleoside or deoxynucleotide, used in each of Examples 17 to 24 was prepared according to the procedure of Example 1. Table 4 shows $^1$H NMR spectrum of compound (I) used in Examples 17 to 21. The spectrum of compound (I) used in Examples 22 to 24 was shown in Tables 1 and 2 above.

TABLE 3

| Example No. | Starting compounds | | Reaction time (hr) | Reaction product | | | |
|---|---|---|---|---|---|---|---|
| | Compound (XI) | Compound (I) | | Structural formula | Yield (%) | Rf in TLC* | 1H NMR (CDCl₃, TMS); δ(ppm) |
| 17 | [DMTrO-sugar-T with O-P(=O)(O-2-chlorophenyl)-N(triazole)] | [Et₃SnO-sugar-T·HNEt₂ with OBz] | 3 | [DMTrO-sugar-T-O-P(=O)(O-2-chlorophenyl)-O-sugar-T-OBz] | 91 | 0.57 | 1.40 (s, 3H,5-CH₃), 1.82(s,3H,5-CH₃),2.10–2.90(m,4H,2' & 2'), 3.10–3.65(m,2H,5'), 3.66(s,6H,OCH₃ & OCH₃), 4.05–4.70(m,4H,4',4' & 5'), 5.20–5.60(m, 2H,3' & 3'), 6.38(t, 2H,J=7.0Hz,1' & 1'), 6.60–6.90(m,4H,Ph), 6.90–7.70(m,18H,6,6 & Ph), 7.85–8.00(m, 2H,Ph) and 9.88(s,2H, NH) |
| 18 | [DMTrO-sugar-T with O-P(=O)(O-2-chlorophenyl)-N(tetrazole)] | [Et₃SnO-sugar-T·HNEt₂ with OBz] | 0.5 | [DMTrO-sugar-T-O-P(=O)(O-2-chlorophenyl)-O-sugar-T-OBz] | 95 | 0.57 | The spectrum was the same as that given in Example 17 |

TABLE 3-continued
| Example | Starting compounds | | Reaction time | Reaction product | | | |
|---|---|---|---|---|---|---|---|
| No. | Compound (XI) | Compound (I) | (hr) | Structural formula | Yield (%) | Rf in TLC* | 1H NMR (CDCl₃, TMS); δ(ppm) |
| 19 | 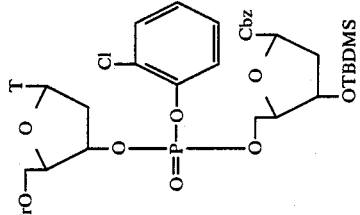 |  | 2 | 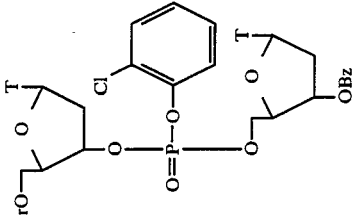 | 92 | 0.57 | The spectrum was the same as that given in Example 17. |
| 20 |  |  | 1 |  | 93 | 0.64 | 0.06(s,6H,Si(CH₃)₂),0.95 (s,9H,SiC(CH₃)₃),1.83(s 3H,5-CH₃),1.90-2.85(m, 4H,2' & 2"),3.20-3.60(m, 2H,5'),3.70(s,6H,OCH₃ & OCH₃),3.90-4.55(m,5H,3', 4',4" & 5"),5.20-5.40(m, 1H,3"),6.15(t,1H,J=7.0 Hz,1'),6.36(t,1H,J=7.0 Hz,1"),6.65-6.90(m,4H, Ph),6.95-7.65(m,17H,6 & Ph),7.70-7.90(m,2H,Ph), 7.96(d,1H,J=7.0Hz,5), 8.52(d,1H,J=7.0Hz,6), 8.94(bs,1H,NH) and 9.47 (s,1H,NH) |

TABLE 3-continued

| | Starting compounds | | Reaction time (hr) | Reaction product | | | |
|---|---|---|---|---|---|---|---|
| Example No. | Compound (XI) | Compound (I) | | Structural formula | Yield (%) | Rf in TLC* | 1H NMR (CDCl₃, TMS); δ(ppm) |
| 21 | DMTrO—[T nucleoside]—O—P(=O)(O-2-chlorophenyl)—N(triazole) | Et₃SnO—[Abz nucleoside]—OBz · HNEt₂ | 1 | DMTrO—[T]—O—P(=O)(O-2-chlorophenyl)—O—[Abz]—OBz | 95 | 0.59 | 1.28(s,1.5H,5-CH₃),1.30 (s,1.5H,5-CH₃),2.20–3.40 (m,6H,2′ & 5′),3.60 (s,6H,OCH₃ & OCH₃),4.00– 4.60(m,4H,4′ & 5′), 5.10–5.40(m,1H,3′),5.50– 5.80(m,1H,3′),6.10–6.60 (m,2H,1′ & 1′),6.60–6.80 (m,4H,Ph),6.80–7.60(m, 20H,6 & Ph),7.80–8.10 (m,4H,Ph),8.22(s,0.5H,2), 8.28(s,0.5H,2),8.68(s,1H, 8),9.86(s,1H,NH),10.40 (s,0.5H,NH) and 10.68 (s,0.5H,NH) |
| 22 | DMTrO—[T nucleoside]—O—P(=O)(O-2-chlorophenyl)—N(triazole) | Et₃SnO—[Cbz nucleoside]—OTBDMS · HNEt₂ | 1 | DMTrO—[T]—O—P(=O)(O-2-chlorophenyl)—O—[Cbz]—OTBDMS | 95 | 0.64 | The spectrum was the same as that given in Example 20. |

TABLE 3-continued

| Example No. | Starting compounds | | Reaction time (hr) | Reaction product | | |
|---|---|---|---|---|---|---|
| | Compound (XI) | Compound (I) | | Structural formula | Yield (%) | Rf in TLC* | 1H NMR (CDCl₃, TMS); δ(ppm) |
| 23 | DMTrO—[structure with T, O, P(=O)(O-2-Cl-phenyl), N-triazole] | Et₃SnO—[structure with Gib, O, HNEt₂, OBz] | 1 | DMTrO—[structure with T, O, P(=O)(O-2-Cl-phenyl), O, Gib, OBz] | 93 | 0.47, 0.52 | 0.80–1.25(m,6H,—CH—(CH₃)₂),1.36(s,1.5H,5-CH₃),1.38(s,1.5H,5-CH₃),2.20–3.60(m,7H,2',2',5' & —CH<),2.65(s,6H,OCH₃ & OCH₃),4.00–4.90(m,4H,4' & 5'),5.05–5.30(m,1H,3'),5.30–5.65(m,1H,3'),6.05–6.50(m,2H,1' & 1'),6.60–6.85(m,4H,Ph),6.85–7.55(m,17H,6 & Ph),7.60(s,0.5H,8),7.66(s,0.5H,8),7.80–8.00(m,2H,Ph),9.58(s,1H,NH),9.98(s,0.5H,NH),10.36(s,0.5H,NH),11.84(s,0.5H,NH) and 12.06(s,0.5H,NH) |
| 24 | DMTrO—[structure with T, O, P(=O)(O-2-Cl-phenyl), N-triazole] | Et₃SnO—[structure with T, O, HNEt₂, P(=O)(O-2-Cl-phenyl), O, T, OTBDMS] | 1 | DMTrO—[structure with T, O, P(=O)(O-2-Cl-phenyl), O, T, O, P(=O)(O-2-Cl-phenyl), O, T, OTBDMS] | 94 | 0.78 | 0.06(s,6H,Si(CH₃)₂),0.94(s,9H,SiC(CH₃)₃),1.37(s,3H,5-CH₃),1.70–2.00(m,6H,5-CH₃),2.00–2.80(m,6H,2',2' & 2'),3.05–3.50(m,2H,5'),3.70 s,6H,OCH₃ & OCH₃),3.95–4.70(m,8H,3',4',4',4' 5' & 5'),5.10–5.45(m,2H,3 & 3'),6.05–6.60(m,3H,1',1' & 1'),6.60–6.90(m,4H,Ph),6.90–7.60(m,20H,6,6,6 & Ph) and 9.72(bs,3H,NH,NH & NH) |

*Eluent: CHCl₃:MeOH = 10:1 by volume

TABLE 4

| Example No. | Compound (I) | $^1$H NMR (CD$_2$Cl$_2$,TMS): δ (ppm) |
|---|---|---|
| 17–19 | Et$_3$SnO—[sugar, O, T, HNEt$_2$, OBz] | 1.09(t,6H,J=7.0Hz,N(CH$_2$CH$_3$)$_2$), 1.30(s,15H,Sn(C$_2$H$_5$)$_3$),1.89(s, 3H,5-CH$_3$),2.36–2.82(m,6H,with a quadruplet at 2.63,J=7.0Hz, 2' & N(CH$_2$ CH$_3$)$_2$),3.80–4.10(m, 2H,5'),4.15–4.40(m,3H,with a singlet at 4.28,4',HNEt$_2$ & NH), 5.50–5.65(m,1H,3'),6.44(t,1H, J=7.0Hz,1'),7.30–7.70(m,3H,Ph), 7.78(s,1H,6),7.95–8.10(m,2H,Ph) |
| 20 | n-Bu$_3$SnO—[sugar, O, Cbz, HNEt$_2$, OTBDMS] | 0.10(s,6H,Si(CH$_3$)$_2$),0.80–1.20 (m,24H,with a singlet at 0.92 and a triplet at 1.05,J=7.0Hz, SiC(CH$_3$)$_3$,Sn(CH$_2$CH$_2$CH$_2$CH$_3$)$_3$, N(CH$_2$CH$_3$)$_2$),1.20–1.80(m,18H, Sn(CH$_2$CH$_2$CH$_2$CH$_3$)$_3$),2.05–2.70 (m,6H,with a quadruplet at 2.60, J=7.0Hz, 2' & N(CH$_2$ CH$_3$)$_2$),3.60– 4.20(m,3H,4' & 5'),4.40–4.70 (m,3H,with a singlet at 4.48 3',HNEt$_2$ & NH),6.22(t,1H,J=6.0Hz, 1'),7.14(d,1H,J=7.0Hz,5), 7.25– 7.65(m,3H,Ph),7.90–8.10(m,2H, Ph) and 8.66(d,1H,J=7.0Hz,6) |
| 21 | Et$_3$SnO—[sugar, O, Abz, HNEt$_2$, OBz] | 0.80–1.40(m,21H,with a triplet at 1.02,J=7.0Hz,N(CH$_2$ CH$_3$)$_2$ & Sn(C$_2$H$_5$)$_3$,2.30–3.00(m,6H,with a quadruplet at 2.58,J=7.0Hz, 2' & N(CH$_2$CH$_3$)$_2$, 3.36(s,2H, HNEt$_2$ & NH),3.80–4.10(m,2H,5'), 4.10–4.35(m,1H,4'),5.50–5.70 (m,1H,3'),6.40–6.60(m,1H,1'), 6.90–7.65(m,8H,Ph),7.80–8.00 (m,2H,Ph),8.20–8.50(m,2H,with a singlet at 8.44,2 & 8) |

EXAMPLE 25

To a methylene chloride solution of 5'-O-dimethoxytrityl-thymidine-3'-O-(2-chlorophenyl)phosphoro-1,2,4-triazolide (0.8M, 0.3 ml, 0.24 mmol) which was prepared in the same manner as in Example 16 was added at 20° C. diethylamine salt of 5'-O-triethylstannyl-3'-O-t-butyldimethylsilyl-thymidine which was prepared by reacting (diethylamino)triethylstannane (0.058 g, 0.05 ml, 0.21 mmol) with 3'-O-t-butyldimethylsilyl-thymidine (0.071 g, 0.2 mmol) for 15 minutes under stirring. Immediately thereafter, diisopropylamine (0.101 g, 0.14 ml, 1 mmol) was added to the mixture and the reaction was conducted at that temperature for 5 minutes. The completion of the reaction was confirmed by TLC, at which a 50% aqueous pyridine solution (0.5 ml) was added to the reaction mixture. The resulting mixture was washed with a 0.5M aqueous potassium primary phosphate solution (10 ml) and a 0.1M aqueous triethylammonium bicarbonate buffer (pH 7.5, 10 ml), successively, and distilled in vacuo to remove the methylene chloride. The residue was subjected to a silica gel (10 g)column chromatography using chloroform-methanol (40:1 by volume) as an eluent. The eluate was concentrated and the residue was dissolved in a small amount of methylene chloride. The resulting solution was added dropwise to n-hexane under vigorous stirring to deposit white crystals which were separated by filtration and dried to yield o-chlorophenyl 5-O-(dimethoxytrityl)thymidine-3'3'-O-(t-butyldimethylsilyl)-thymidine-5' phosphate (0.204 g). Yield: 95% based on 5'-O-triethylstannyl-3'-O-t-butyldimethylsilyl-thymidine. Rf value in TLC (chloroform:methanol=10:1) and $^1$H NMR spectrum (CDCl$_3$, TMS) of the product are the same as those of the product of Example 16.

EXAMPLES 26–31

The procedure of Example 25 was repeated using various 3'-O-phosphoro-1,2,4-triazolide derivatives of deoxynucleosides and various 5'-O-triorganostannyl derivatives of deoxynucleosides or deoxynucleotides as shown in Table 5, affording corresponding dideoxynucleotides and trideoxynucleotides as given in Table 5. Each of the reaction product obtained in Examples 26–31 was confirmed to have Rf value in TLC (eluent: CHCl$_3$:MeOH=10:1 by volume) and $^1$H NMR spectrum corresponding with those given in Table 3 for the same compound.

TABLE 5
| Example No. | Starting compounds | | Catalyst | Reaction time (min) | Reaction product Structural formula | Yield |
|---|---|---|---|---|---|---|
| | Compound (X) | Compound (I) | | | | |
| 26 | 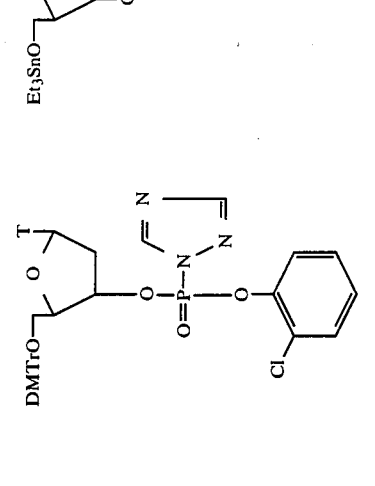 | 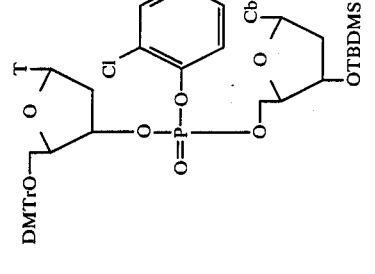 | 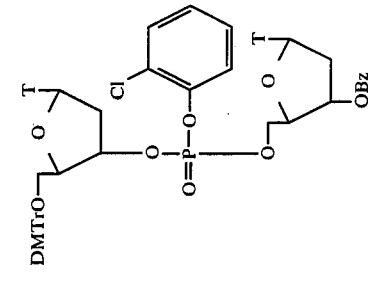 | 5 | 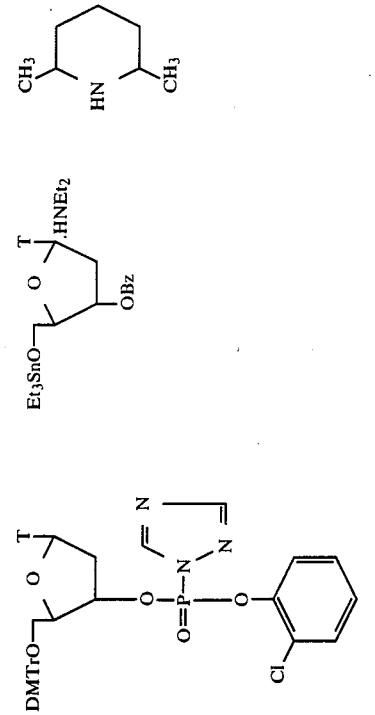 | 94% |
| 27 |  | 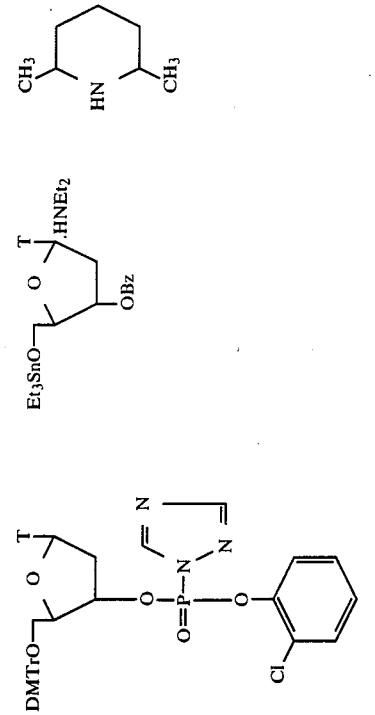 | HN(i-Pr)$_2$ | 5 | | 95% |

TABLE 5-continued

| Example No. | Starting compounds | | | Catalyst | Reaction time (min) | Reaction product | |
|---|---|---|---|---|---|---|---|
| | Compound (X) | Compound (I) | | | | Structural formula | Yield |
| 28 | DMTrO-[sugar-T]-O-P(=O)(O-2-Cl-C₆H₄)-N(triazole) | Et₃SnO-[sugar-Cbz]-OTBDMS, HNEt₂ | | 2,2,6,6-tetramethylpiperidine | 5 | DMTrO-[sugar-T]-O-P(=O)(O-2-Cl-C₆H₄)-O-[sugar-CBz]-OTBDMS | 94% |
| 29 | DMTrO-[sugar-T]-O-P(=O)(O-2-Cl-C₆H₄)-N(triazole) | Et₃SnO-[sugar-Abz]-OBz, HNEt₂ | | 2,6-dimethylpiperidine | 5 | DMTrO-[sugar-T]-O-P(=O)(O-2-Cl-C₆H₄)-O-[sugar-Abz]-OBz | 95% |

TABLE 5-continued

| Example No. | Starting compounds | | | Catalyst | Reaction time (min) | Reaction product | |
|---|---|---|---|---|---|---|---|
| | Compound (X) | Compound (I) | | | | Structural formula | Yield |
| 30 | [structure: DMTrO-T-nucleoside with O-P(=O)(O-2-chlorophenyl)-N(triazole)] | [structure: Et₃SnO-Gib-nucleoside-OBz · HNEt₂] | | 2,6-dimethylpiperidine (CH₃-NH-CH₃) | 10 | [structure: DMTrO-T-O-P(=O)(O-2-Cl-C₆H₄)-O-Gib-OBz dinucleotide] | 94% |
| 31 | [structure: DMTrO-T-nucleoside with O-P(=O)(O-2-chlorophenyl)-N(triazole)] | [structure: Et₃SnO-T-O-P(=O)(O-2-Cl-C₆H₄)-O-T-OTBDMS · HNEt₂] | | 2,6-dimethylpiperidine (CH₃-NH-CH₃) | 10 | [structure: DMTrO-T-O-P(=O)(O-2-Cl-C₆H₄)-O-T-O-P(=O)(O-2-Cl-C₆H₄)-O-T-OTBDMS trinucleotide] | 95% |

What we claim is:

1. A triorganostannyl derivative of a deoxynucleoside or deoxynucleotide of the formula (I):

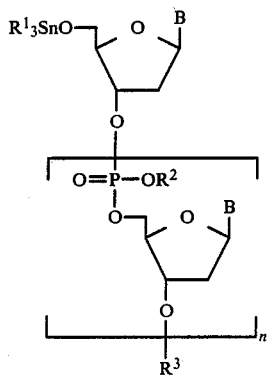

wherein $R^1$ is a lower alkyl or phenyl, $R^2$ is o-chlorophenyl or p-chlorophenyl, $R^3$ is acetyl, benzoyl or t-butyldimethylsilyl, B is a thymine, $N^2$-isobutyrylguanine, $N^4$-benzoylcytosine or $N^6$-benzoyladenine moiety, and n is zero or a positive integer, or a lower alkylamine salt thereof.

2. A compound according to claim 1 wherein $R^1$ is a lower alkyl group of 1–4 carbon atoms.

3. A compound according to claim 1 which is selected from:
5′-O-triethylstannyl-3′-O-t-butyldimethylsilyl-thymidine and a dialkylamine salt thereof;
5′-O-triethylstannyl-3′-O-acetyl-thymidine and a dialkylamine salt thereof;
5′-O-tri-n-butylstannyl-3′-O-t-butyldimethylsilylthymidine and a dialkylamine salt thereof;
5′-O-triethylstannyl-3′-O-t-butyldimethylsilyl-$N^2$-isobutyryldeoxyguanosine and a dialkylamine salt thereof;
5′-O-triethylstannyl-3′-O-t-butyldimethylsilyl-$N^4$-benzoyldeoxycytidine and a dialkylamine salt thereof;
5′-O-triethylstannyl-3′-O-t-butyldimethylsilyl-$N^6$-benzoyldeoxyadenosine and a dialkylamine salt thereof;
o-chlorophenyl 5′-O-(triethylstannyl)thymidine-3′3′-O-(t-butyldimethylsilyl)thymidine-5′ phosphate and a dialkylamine salt thereof;
5′-O-trimethylstannyl-3′-O-t-butyldimethylsilylthymidine and a dialkylamine salt thereof;
5′-O-trimethylstannyl-3′-O-t-butyldimethylsilyl-$N^4$-benzoyldeoxycytidine and a dialkylamine salt thereof; and
5′-O-triethylstannyl-3′-O-benzoyl-$N^2$-isobutyryldeoxyguanosine and a dialkylamine salt thereof.

* * * * *